(12) United States Patent
Ferrari

(10) Patent No.: US 7,850,592 B2
(45) Date of Patent: Dec. 14, 2010

(54) DEVICE FOR THE EPICARDIAL SUPPORT AND/OR RESUMPTION OF CARDIAC ACTIVITY

(75) Inventor: Markus Ferrari, Jena (DE)

(73) Assignee: PPA Technologies AG, Jena (DE)

( * ) Notice: Subject to any disclaimer, the term of this patent is extended or adjusted under 35 U.S.C. 154(b) by 882 days.

(21) Appl. No.: 11/569,044

(22) PCT Filed: May 10, 2005

(86) PCT No.: PCT/EP2005/005052

§ 371 (c)(1),
(2), (4) Date: Nov. 13, 2006

(87) PCT Pub. No.: WO2005/110513

PCT Pub. Date: Nov. 24, 2005

(65) Prior Publication Data

US 2007/0191672 A1    Aug. 16, 2007

(30) Foreign Application Priority Data

May 11, 2004   (DE) ................. 10 2004 023 192

(51) Int. Cl.
*A61N 1/362* (2006.01)
(52) U.S. Cl. ........................................... 600/16
(58) Field of Classification Search ............ 600/16; 607/3
See application file for complete search history.

(56) References Cited

U.S. PATENT DOCUMENTS

| 3,034,501 | A |   | 5/1962  | Hewson |
| 3,513,836 | A |   | 5/1970  | Sausse |
| 5,169,381 | A |   | 12/1992 | Snyders |
| 5,697,951 | A | * | 12/1997 | Harpstead et al. ............. 607/3 |
| 5,738,627 | A |   | 4/1998  | Kovacs et al. |
| 6,579,223 | B2 | * | 6/2003 | Palmer ....................... 600/16 |
| 7,468,029 | B1 | * | 12/2008 | Robertson, Jr. ............. 600/37 |

FOREIGN PATENT DOCUMENTS

DE           19951220 A1     4/2001

* cited by examiner

*Primary Examiner*—George Manuel
*Assistant Examiner*—Robert N Wieland
(74) *Attorney, Agent, or Firm*—Roberts Mlotkowski Safran & Cole, P.C.; David S. Safran

(57) ABSTRACT

A device for epicardial support and/or the assuming of cardiac activity having a double membrane (1) consisting of an elastic inner membrane (2) and a non-expandable outer membrane (3) as well as a closed cavity (4) formed therebetween which can be inflated and deflated by means of a fluid exhibiting a first chamber (6) allocated to the right ventricle (5) and a second chamber (8) allocated to the left ventricle (7). With the objective of further developing a device of the type indicated so that it provides for simple device operability while maintaining the advantage of being able to augment only one ventricle, it is provided for the first chamber (6) and the second chamber (8) are connected to one another by at least one valve (9) in a dividing wall (10) separating the two chambers (6, 8).

4 Claims, 3 Drawing Sheets

DEVICE FOR THE EPICARDIAL SUPPORT AND/OR RESUMPTION OF CARDIAC ACTIVITY

BACKGROUND OF THE INVENTION

1. Field of the Invention

The present invention relates to a device for epicardial support and/or the assuming of cardiac activity having a double membrane consisting of an elastic inner membrane and a non-expandable outer membrane as well as a closed cavity formed therebetween which can be inflated and deflated by means of a fluid exhibiting a first chamber allocated to the right ventricle and a second chamber allocated to the left ventricle.

2. Description of Related Art

Such a device—although one which works pericardially—is known for example from the document DE 199 51 220 A1. The device is a minimally-invasive, i.e. percutaneously implantable system for the mechanical support and temporary substitution of the heart's pumping function. After probing the pericardial sac, the device is inserted into the pericardial sac percutaneously in collapsed state or surgically positioned in the pericardial sac at the end of an operation with the double membrane surrounding the right and left ventricles. The device in its deflated state is so thin that a compression of the adjacent organs will be avoided. Subsequent implantation, the cavity of the double membrane is rhythmically supplied through a connecting tube with a fluid which can either be a gas (helium or $CO_2$) or a suitable liquid. Due to this rhythmic inflation and deflation of the double membrane's cavity and because the outer membrane is not expandable in contrast to the inner membrane, the double membrane surrounding the heart effects pressure transmission and compression of the heart. In so doing, blood is urged from the right ventricle into the pulmonary artery and simultaneously from the left ventricle into the aorta or, when the heart is pumping, aids in the systolic ejection of the cardiac muscle.

A device for supporting cardiac activity is known from U.S. Pat. No. 5,169,381 A which has a double membrane comprising an inner and an outer membrane as well as a closed cavity formed therebetween which can be inflated and deflated by means of a fluid. This double membrane has an axially-extending wedge-shaped slot spanning ¾ of the vertical extension of the double membrane and is furthermore provided with a first chamber allocated to the right ventricle and a second chamber allocated to the left ventricle. Each of these two chambers are supplied with fluid separately, which entails a double expenditure of fluid tubes and valves and results in the device as a whole being relatively complicated in its operation.

Against the background of the disadvantages of the latter device for supporting cardiac activity as described, the task on which the present invention is based is that of providing simple operability of the device while maintaining the advantage of being able to augment only one ventricle.

SUMMARY OF THE INVENTION

This object is solved by a device for the epicardial support of cardiac activity of the type as indicated at the outset according to the invention in that the first chamber and the second chamber are connected to one another by means of at least one valve in a dividing wall separating the two chambers.

The advantage of the device according to the invention is in particular in that only one fluid tube is required to inflate and deflate the cavity of the double membrane and yet one ventricle can still be augmented by regional inflation/deflation. The device thus formulated is simple to operate and depending on need, double membranes can be produced which allow the exclusive augmentation of the right ventricle or—in another embodiment—only the left ventricle, both while maintaining the potential to simultaneously support both ventricles.

The inventive type of chambering and mechanical modification of the double membrane by at least one internal valve thus enables an isolated augmentation of a single ventricle, whereby the double membrane surrounds the other ventricle for purposes of mechanical stabilization and hence contributes stabilization in the sense of a support. Thus, in the event of isolated right ventricular failure, a primary augmentation of the right ventricle can follow, while the double membrane only passively wraps the left ventricle. Opening or closing the valve enables switching between the two operating modes thus given; i.e. "full augmentation" or "regional augmentation".

The valve which connects the two chambers together and which is arranged in the dividing wall separating the two chambers is preferably externally opened and closed in a controlled manner. That means that the valve can be operated for example by means of an IR signal or by means of a radio signal. The advantage to this further development is that there is then no need for an additional control line for the valve, hence avoiding a further risk for the patient.

Since external compression of the epicardial vessels is undesirable after coronary bypass surgery, the double membrane near the large coronary artery preferably comprises variable recesses. Such a of double membrane can either be custom-made for a patient or, however, as a further advantageous embodiment provides, customized to the particular requirements of a patient's heart by means of displaceable supports. The variable recesses can thereby be brought into their desired position by the surgeon mechanically manipulating collapsible flexible bars or half-tubes. These collapsible flexible bars or half-tubes can be held in the desired position during pumping either by their own self-adhering properties, the use of a tissue adhesive, by a support rail or by grooves within the double membrane which force specific positions.

The following will make reference to a figure in describing an embodiment of the invention in greater detail.

DETAILED DESCRIPTION OF THE INVENTION

Figure 1:
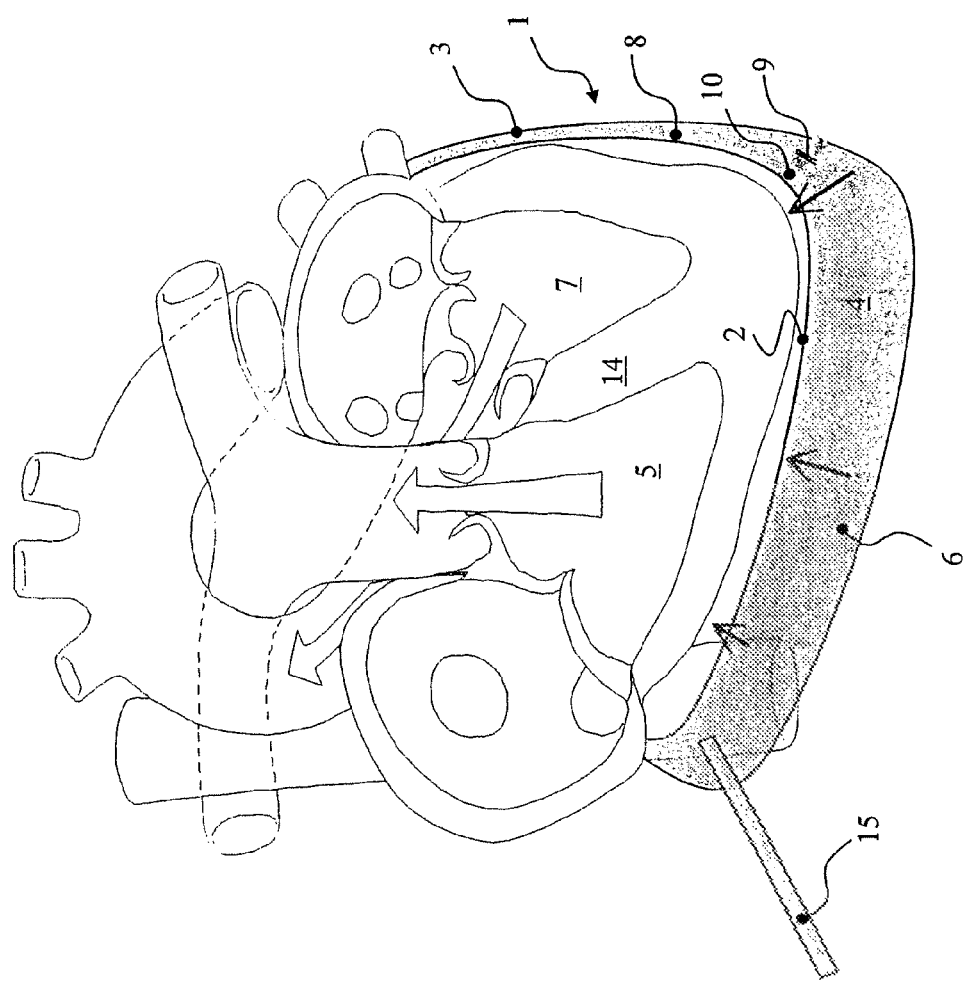
FIG. 1: a schematic representation of the device according to the invention with augmentation of only the right ventricle in the systolic phase.

FIG. 1 shows a schematic representation of a device for epicardial support and/or the assuming or resuming of cardiac activity having a double membrane 1 consisting of an elastic inner membrane 2 and a non-expandable outer membrane 3 as well as a closed cavity 4 formed therebetween which can be inflated and deflated by means of a fluid through fluid tube 15. Cavity 4 is divided into a first chamber 6 allocated to the right ventricle 5 and a second chamber 8 allocated to the left ventricle 7 by a dividing wall 10. Both chambers 6, 8 are connected together by means of at least one valve 9 arranged in the dividing wall 10. Valve 9 or all the valves arranged in the dividing wall respectively (only one is depicted here) can thereby be externally opened and closed in a controlled manner, for example by IR or radio signal.

The three arrows within the inflated chamber 6 of the right ventricle 5 pointing inward toward the heart 14 indicate that the representation reflects a snapshot of the systolic phase with augmentation of only the right ventricle 5 by regional inflation of double membrane 1.

Figure 2:
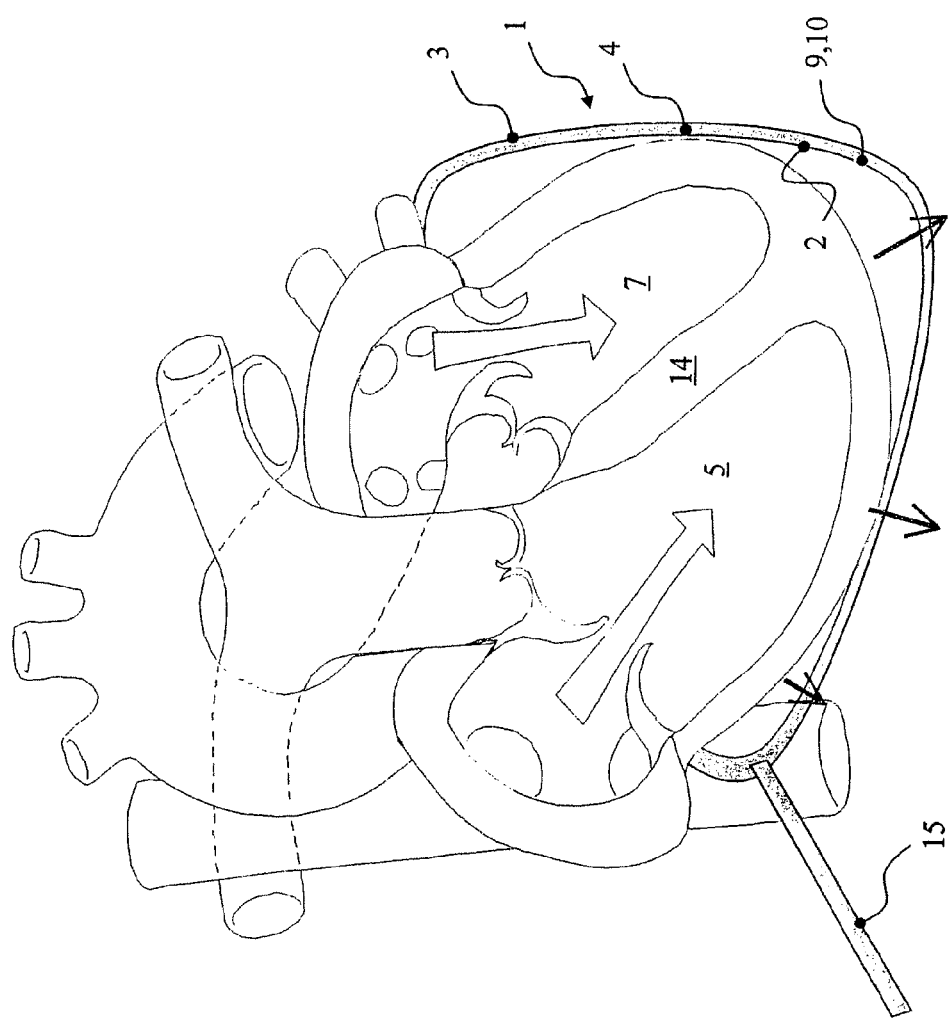
FIG. 2: a comparable representation to FIG. 1 in the diastolic phase.

FIG. 2 shows a representation comparable to that of FIG. 1 in the diastolic phase. Here the filling of the right ventricle 5 is augmented by the deflation of the right chamber 6 of double membrane 1. In cases where only an augmentation of the right ventricle 5 is desired, the valve 9 in dividing wall 10 remains closed. Only when an augmentation of both ventricles 5, 7 is desired is both the first chamber 6 as well as also the second chamber 8 then inflated/deflated.

Figure 3:
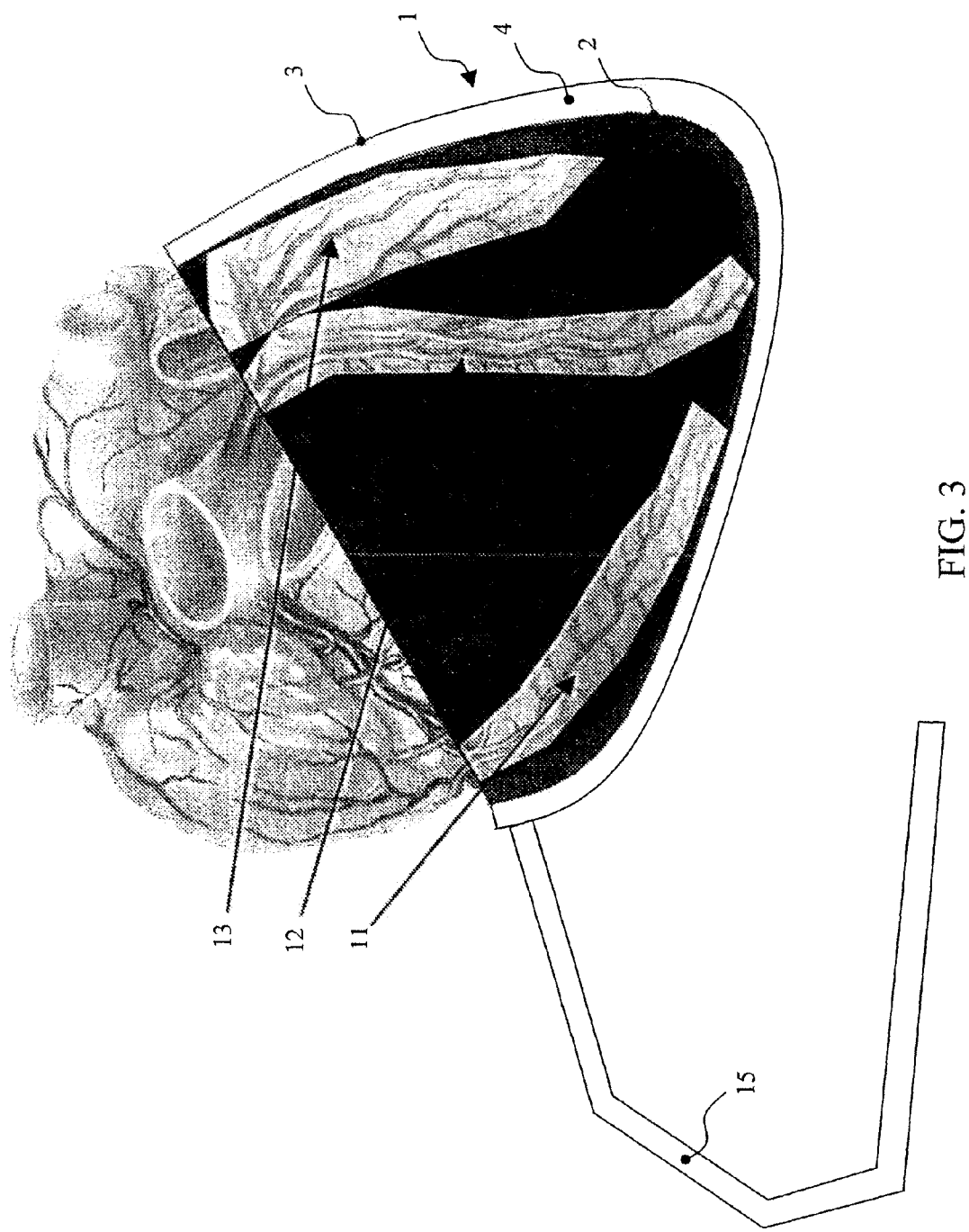
FIG. 3: a representation of the human heart with the inserted device and recesses.

FIG. 3 shows the heart of a patient with a schematically-depicted surrounding double membrane 1, the cavity 4 of which is in turn inflatable and deflatable by means of the fluid tube 22. This embodiment of double membrane 1 exhibits variable recesses 11, 12, 13 in the area of the large coronary artery in order to avoid external compression of the epicardial vessels. These recesses 11, 12, 13 are customizable to the specific requirements of a patient's heart by means of displaceable supports which are not shown here.

What is claimed is:

1. A device for at least one of epicardial support and assuming of cardiac activity, comprising:
   a double membrane formed of an elastic inner membrane and a non-expandable outer membrane with a closed cavity being formed therebetween which is inflatable and deflatable by means of a fluid, the closed cavity having a first chamber which is allocatable, in use, to a patient's right ventricle and a second chamber which is allocatable, in use, to a patient's left ventricle, the chambers being separated by a dividing wall;
   wherein the first chamber and the second chamber are connected to one another by means of at least one valve in the dividing wall separating the two chambers, wherein a fluid tube for fluidically inflating and deflating said chambers is connected to said first chamber and wherein inflation and deflation of the second chamber is controlled by said at least one valve,
   wherein the fluid tube is connected only to the first chamber, wherein the at least one valve selectively fluidly connects the two chambers, wherein the device is operable in first and second modes, wherein in the first mode the at least one valve is controlled open and both chambers are configured for inflation and deflation through the fluid tube, and wherein in the second mode the at least one valve is controlled closed and only the first chamber is configured for inflation and deflation through the fluid tube while the second chamber is isolated.

2. The device according to claim 1, wherein at least one valve is externally opened and closed in a controlled manner.

3. The device according to claim 1, wherein recesses are provided in the double membrane in an area which, in use, is in an area of a patient's large coronary artery.

4. The device according to claim 3, wherein displaceable supports are provided by means of which the recesses are adaptable to requirements of a particular patient's heart.

* * * * *